(12) United States Patent
Dosenbach et al.

(10) Patent No.: US 6,423,722 B1
(45) Date of Patent: Jul. 23, 2002

(54) CRYSTALLINE MACROLIDES AND PROCESS FOR THEIR PREPARATION

(75) Inventors: Cornelia Dosenbach, Efringen-Kirchen (DE); Maximilian Grassberger, Vienna (AT); Otto Hartmann, Basel (CH); Amarylla Horvath, Vienna (AT); Jean-Paul Mutz, Blotzheim (FR); Gerhard Penn, Oberwil (CH); Sabine Pfeffer, Weil; Dierk Wieckhusen, Binzen, both of (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/690,404

(22) Filed: Oct. 17, 2000

Related U.S. Application Data

(63) Continuation of application No. 09/446,217, filed as application No. PCT/EP98/03929 on Jun. 26, 1998.

(30) Foreign Application Priority Data

Jun. 30, 1997 (GB) .............................. 9713730

(51) Int. Cl.[7] ..................... A61K 31/695; C07D 498/16
(52) U.S. Cl. ..................... 514/291; 514/183; 514/411; 540/456
(58) Field of Search ................... 514/183, 291, 514/411; 540/456

(56) References Cited

U.S. PATENT DOCUMENTS

| | | | |
|---|---|---|---|
| 4,127,647 A | | 11/1978 | Toshiyuki et al. |
| 5,143,918 A | * | 9/1992 | Bochis et al. ............... 514/291 |
| 5,344,833 A | | 9/1994 | Hughes ....................... 514/291 |
| 5,344,925 A | | 9/1994 | Goulet et al. ................ 540/456 |
| 5,508,398 A | * | 4/1996 | Gletos ........................ 540/456 |

FOREIGN PATENT DOCUMENTS

| | | |
|---|---|---|
| EP | 0 427 680 A | 5/1991 |
| EP | 0 480 623 A | 4/1992 |
| EP | 0 526 171 A2 | 2/1993 |
| EP | 0 433 428 B1 | 10/1994 |
| EP | 0 652 219 A | 5/1995 |
| GB | 2 084 580 A | 1/1992 |
| WO | WO 91 13889 A | 9/1991 |
| WO | WO 95 22390 A | 8/1995 |
| WO | WO 97 08182 A | 3/1997 |

OTHER PUBLICATIONS

Pavia et al. "Introduction to organic laboratory techniques" Saunders Publ. (1988) p. 481–489. copies in parent case.*
Giron, D.—Thermal Analysis and Calorimetric Methods in the Characterisation of Polymorphs and Solvates—Thermochim. Acta, vol. 248, 1995, pp. 1–59.

Chemical Abstracts, vol. 114, No. 5, Feb. 4, 1991, Abstract No. 43482y, H. Murata et al.—Purification of Macrolide Antibiotis by Crystallization from Aqueous Solution, p. 812.

Meingassner, et al. A novel anti–inflammatory drug, SDZ, ASM 981, for the topical and oral treatment of skin diseases: in vivo pharmacology, British Journal of Dermatology, 137: 568–576, 1997.

Tanaka et al., (CA 107:175741, abstract of J. Am. Chem. Soc. (1987), 109(16), 5031–3.

Taga et al., (CA 107:236308, abstract of Acta Crystallogr., Sect. C: Cryst. Struct. Commun. (1987), C43(4), 751–3.

* cited by examiner

*Primary Examiner*—Ceila Chang
(74) *Attorney, Agent, or Firm*—Carol A. Loeschorn

(57) ABSTRACT

33-Epichloro-33-desoxyascomycin of formula I

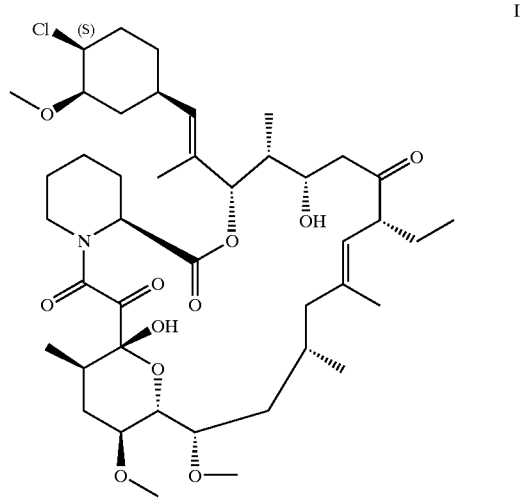

and various tautomeric or forms thereof, in crystalline form, such as Form A and Form B.

Their preparation involves appropriately converting amorphous compound of formula I, or compound of formula I in other than Form A, or compound of formula I in other than Form B, respectively, from a solution thereof under crystallization-inducing conditions or conditions inducing preferential crystallization of Form A or B, respectively.

Such crystals are particularly indicated for use in the preparation of topical galenical forms of the compound for pharmaceutical use, e.g. creams, emulsions and ointments.

8 Claims, 7 Drawing Sheets

CRYSTALLINE MACROLIDES AND PROCESS FOR THEIR PREPARATION

This is a continuation of Ser. No. 09/446,217, Dec. 16, 1999, pending, which is a 371 of PCT/EP98/03929, Jun. 26, 1998, pending.

The invention relates to macrolide chemistry. It concerns the compound of formula I

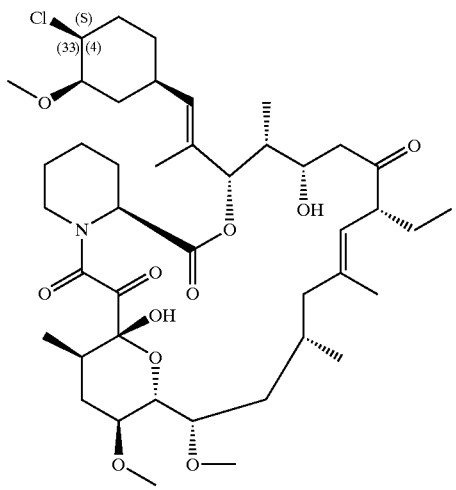

i.e. {[1E-(1R,3R,4S)]1R,9S,12S,13R,14S,17R,18E,21S, 23S,24R,25S,27R}-12-[2-(4-chloro-3-methoxycyclohexyl)-1-methylvinyl]-17-ethyl-1,14-dihydroxy-23,25-dimethoxy-13,19,21,27-tetramethyl-11,28-dioxa-4-azatricyclo[22.3.1.0 (4,9)]octacos-18-ene-2,3,10,16-tetraone, hereinafter briefly named "33-epichloro-33-desoxy-FR520" or "33-epichloro-33-desoxyascomycin", in crystalline form.

For simplicity, formula I as referred to herein should be understood as including the compound of formula I in the various tautomeric forms with which it is in equilibrum, particularly in solution, and solvated, e.g. hydrated forms, such as the tautomeric forms of formula

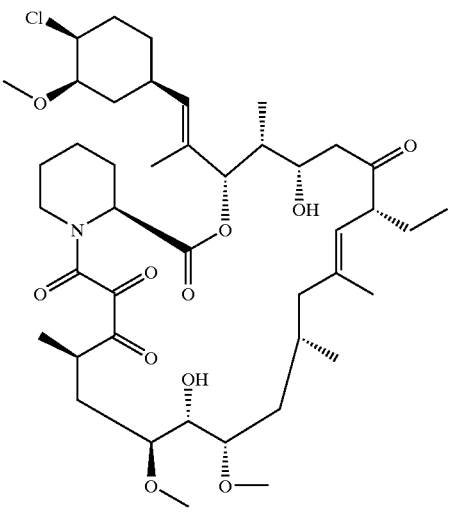

and of formula

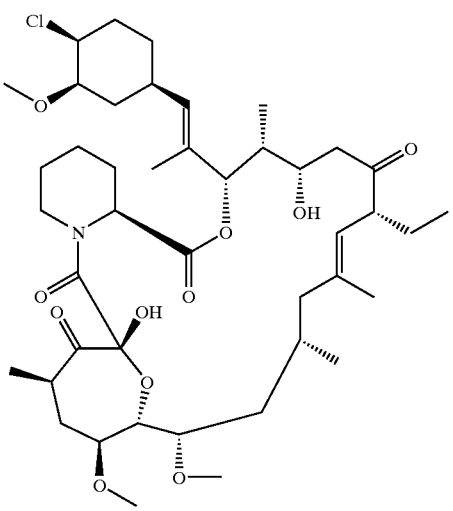

The compound of formula I is known in amorphous form, e.g. from Sandoz EP 427 680, Example 66a in the form of a colourless foamy resin [with $^1$H-NMR=4.56 (m, H-33)], and from Merck EP 480 623, Example 53 (without any physicochemical characterization). Various names and carbon atom numberings are used in the literature.

Prior to the present invention, the compound of formula I had never been recovered in crystalline form.

It appears that the presence of a halogen atom, especially chlorine in the cyclohexyl moiety of the molecule, particularly in the 4 position thereof (also marked as position 33 in formulae I and Ic herein), has an unfavourable effect on the crystallization properties of this structural class of compounds. Thus in EP 427 680 none of the halogenated final products is obtained in crystalline form, they are colourless foams or foamy resins, and characterized by their NMR spectra.

Similarly, in EP 480 623, which covers exclusively macrolide end products halogenated in the cyclohexyl moiety, none of the specific compounds disclosed is characterized by data indicative of crystallinity, such as a melting point; most end products therein are not characterized by any physicochemical data at all, and those that are characterized, are characterized by their mass spectra, which are not indicative as regards physical state; and none of the 4-chloro end products disclosed is characterized at all.

Further analogous macrolides halogenated in the cyclohexyl moiety are also disclosed in e.g. Fisons WO 91/13889, specifically, as Examples 42a), 42b) and 49a): the compounds therein are also not obtained in crystalline form, but recovered as a foam or an oil.

Overall, the 23-membered tricyclomacrolides derived from FK 506 are obtainable in crystalline form only with difficulty, if at all, as appears also from e.g. Merck WO 97/8182, concerning a macrolide compound having a basic substituent capable of forming salts, which could be obtained in crystalline form, but as a tartrate salt. The compound of the present invention is devoid of such a basic substituent.

It is thus surprising that crystallization of the compound of formula I has now been successfully achieved.

The invention concerns the compound of formula I in crystalline form. The crystalline form may appear as solvated, e.g. hydrated, or anhydrous form, or be a tautomer.

While the first recovery of the compound of formula I in crystalline form occurred several years after the first synthesis of the compound, initially obtained only in amorphous form, it has turned out that subsequently to its first crystallization, the compound could be induced to crystallize from the amorphous form quite readily. The crystalline material has thus now become easily accessible, using a variety of experimental conditions extending beyond the initially used recrystallization conditions, which involved the addition of water to an ethanolic solution of the amorphous compound.

The invention also concerns a process for the preparation of the compound of formula I, or a tautomeric or solvated form thereof, in crystalline form which comprises appropriately converting amorphous compound of formula I from a solution thereof under crystallization-inducing conditions.

It also concerns the compound of formula I, or a tautomeric or solvated form thereof, in crystalline form whenever prepared by that process, and the compound of formula I in a non-crystalline, e.g. in dissolved state, or a tautomeric or solvated form thereof, whenever produced from a crystalline form.

The process of the invention is effected in conventional manner. The precise conditions under which crystals are formed may now be empirically determined and a number of methods are suitable in practice, including the initial addition of water to an ethanolic solution of the compound of formula I in amorphous form.

Crystallization-inducing conditions normally involve the use of an appropriate crystallization-inducing solvent, such as methanol, ethanol, isopropanol or water or mixtures thereof. Conveniently, the amorphous compound is dissolved in the solvent at a temperature of normally at least 10° C. The solution may be produced by dissolving in a solvent any one or more of amorphous forms of the compound, and solvates thereof, such as hydrates, methanolates, ethanolates, isopropanolates and acetonitrilates. Crystals may then be formed by conversion from solution, crystallization taking place at a temperature of between about 10° C. and the boiling point of the solvent. The dissolution and crystallization may be carried out in various conventional ways. For instance, amorphous compound may be dissolved in a solvent or a mixture of solvents in which it is readily soluble at elevated temperatures but in which it is only sparingly soluble at lower temperatures. Dissolution at elevated temperature is followed by cooling during which the desired crystals crystallize out of solution. Solvents which are suitable include esters such as methyl acetate and ethyl acetate, toluene and acetonitrile. Mixed solvents comprising a good solvent in which the compound is readily soluble, preferably, in amounts of at least 1% by weight at 30° C., and a poor solvent in which it is more sparingly soluble, preferably in amounts of not more than about 0.01% by weight at 30° C., may also be employed provided that crystallization from the mixture at a reduced temperature, of normally at least about, 10° C., is possible using the selected solvent mixture.

Alternatively, the difference in solubility of the crystals in different solvents may be used. For example, the amorphous compound may be dissolved in a good solvent in which it is highly soluble such as one in which it is soluble in amounts of at least 1% by weight at about 30° C., and the solution subsequently mixed with a poor solvent in which it is more sparingly soluble, such as one in which it is soluble in amounts of not more than about 0.01% by weight at about 30° C. Thus, the solution of the compound in the good solvent may be added to the poor solvent, while maintaining normally a temperature in excess of about 10° C., or the poor solvent may be added to the solution of the compound in the good solvent, again while normally maintaining a temperature in excess of about 10° C. Examples of good solvents include lower alcohols, such as methanol, ethanol and isopropanol, as well as acetone, tetrahydrofuran and dioxane. Examples of poor solvents are water, hexane and diethyl ether. Preferably, crystallization is effected at a temperature in the range of about 10° C. to about 60° C.

In an alternative embodiment of the process of the invention, solid amorphous compound is suspended at a temperature of normally at least about 10° C. in a solvent in which it is incompletely soluble, preferably only sparingly soluble, at that temperature. A suspension results in which particles of solid are dispersed, and remain incompletely dissolved in the solvent. Preferably the solids are maintained in a state of suspension by agitation e.g. by shaking or stirring. The suspension is kept at a temperature of normally about 10° C. or higher in order to effect a transformation of the starting solids into crystals. The amorphous solid compound suspended in a suitable solvent may be a solvate, e.g. hydrate, methanolate, ethanolate, isopropanolate or acetonitrilate. The amorphous powder may be derived by drying a solvate.

It is preferred to add "seeds" of crystalline material to the solution in order to induce crystallization.

The compound of formula I in crystalline form can readily be isolated, it can e.g. be filtered off or centrifuged from the crystallization medium, if desired after cooling, and washed and dried, and optionally further recrystallized using similar conditions.

While the initial recovery has resulted in material in a crystalline form designated as "Form A" herein, surprisingly, it has turned out upon further investigation that at least one additional crystal form of the compound may be recovered, herein designated as "Form B", which differs from Form A in various characteristics, such as its solubility. The invention thus concerns the compound of formula I or a tautomeric or solvated form thereof in crystalline form as such, and more particularly Form A and Form B. Form A is preferred.

Form A normally is in hydrated form at room temperature. The hydrated form can be reversibly dehydrated by heating to about 110° C. It remains in Form A thereby. The hydrated form is the more stable state of Form A at room temperature. Form B normally is not in hydrated form, even at room temperature. It is thermodynamically a more stable form than Form A.

A crystal form is defined herein as being "crystallographically pure" when it contains at most about 0.5% (w/w), e.g. at most about 0.1% (w/w) of other form. Thus e.g. "crystallographically pure Form A" contains about $\leq 0.5\%$ (w/w), .g. about $\leq 0.1\%$ (w/w) of Form B and/or amorphous form.

The preparation of Forms A and B may be effected using conventional means, starting either from amorphous material or from Form B or Form A, respectively, or mixtures thereof. Normally, the starting material is dissolved into an appropriate solvent and crystallized or recrystallized therefrom under conditions preferentially producing either Form A or Form B, resulting in crystallographically pure Form A or Form B.

The invention thus includes a process variant for the preparation of the compound of formula I, or a tautomeric or solvated form thereof, in crystalline Form A which comprises appropriately converting compound of formula I in other than Form A, or a tautomeric or solvated form thereof, from a solution thereof under conditions inducing preferential crystallization of Form A. It also concerns the compound of formula I in Form A whenever prepared by that process variant.

Conversely, the invention includes a process variant for the preparation of the compound of formula I, or a tautomeric or solvated form thereof, in crystalline Form B which comprises appropriately converting compound of formula I in other than Form B from a solution thereof under conditions inducing preferential crystallization of Form B. It also concerns the compound of formula I in Form B whenever prepared by that process variant.

For the preparation of Form A the starting material is conveniently dissolved in an appropriate solvent, preferably ethanol/water, preferably in the proportions 9.5:0.5. The temperature for dissolution is from about 60° C. to about 75° C., preferably about 70° C. The proportion of starting material to solvent preferably is from about 1:5 to about 1:6 on a weight basis, preferably about 1:5 (w/w). The solution is filtered and then cooled to a reduced temperature, preferably of from about 70° C. to about 20° C., preferably about 10° C., and a liquid in which Form A is insoluble, such as water, is carefully added. A supersaturated solution results thereby. While crystals of Form A may spontaneously be formed, preferably the supersaturated solution is seeded with a few crystals of crystallographically pure Form A. It is usually beneficial to check the purity of the seeding crystals with a melt microscope. Further addition of liquid under careful stirring leads to more crystals of Form A. Low temperature, i.e. below about 20° C., and seeding with crystallographically pure crystals of Form A appear to prevent the formation of crystals of Form B. Too lengthy stirring may be counter-productive, particularly at temperatures above 10° C., Form B being the thermodynamically more stable form.

Conveniently, as a preliminary step, the starting material is preferably thoroughly dissolved in a polar organic solvent such as an alcohol, e.g. methanol, ethanol, isopropanol, preferably ethanol, or in acetone, especially in acetone, preferably at boiling temperature, and the solvent evaporated to dryness.

For the preparation of Form B the starting material is again dissolved in a solvent as described above for preparing Form A, preferably ethanol/water 9.5:0.5 (v/v). The temperature for dissolution is again from about 60° C. to about 75° C., preferably about 70° C., and the resultant solution is filtered. The proportion of starting material to solvent is somewhat less than for preparing Form A, it is preferably about 1:7 (w/w). However, cooling is to a higher temperature than when preparing Form B, it is preferably to above 20° C., e.g. to about 25° or 30° C., and the further workup is also effected at about that temperature or a similar temperature. Seeding with crystals of Form B is optional, but greatly facilitates crystallization and allows more latitude as regards e.g. temperature. The speed of formation of the supersaturated solution appears also to exert some effect on the result obtained, speedy supersaturation resulting in increased formation of Form B.

A solvate, e.g. a hydrate, may be converted into the corresponding unsolvated form in conventional manner and vice-versa, e.g. by appropriately heating up the solvated form, or cooling down the unsolvated form of the crystal form susceptible of being solvated.

The two crystal forms identified are characterized i.a. by the following physico-chemical data:

1) Form A:
   appearance: white to off-white, finely crystalline powder (from ethanol/water);
   m.p. determined by DSS (10° K/mir): melting onset at about 132° C.;
   solubility (at 5° C.):
     water: insoluble
     methanol, ethanol, ethyl acetate, diethylether, diisopropyl ether: >100 mg/ml
     hexane: <10 mg/ml;
   solubility (at 25° C.):
     acetone, acetonitrile, ethanol, ethyl acetate, isopropanol, methanol: >50 mg/ml;
     water: <1 mg/ml;
   solubility in the oil phase of cream (oleyl alcohol/miglyol $812^R$ 4:6): 2.49%;
   chemical purity: 98.5%;
   thermogravimetry: loss of mass on drying up to melting: 1.46% (Carl Fischer titration);
   morphology (SEM): sticks and agglomerates (1–100 μm);
   hygroscopicity (uptake determined by thermogravimetry): 1.49% (1 day, 92% r.h.); 1.78% (1 week, 25° C., 75% r.h.);
   DSC curve: see FIG. 1 (Perkin Elmer DSC-7 differential scanning calorimeter; measurement from 40° C. to 200° C., scan heating rate 10° K/min);
   FT-IR spectrum: see FIGS. 3 and 5 (PE FT-IR spectrometer 1725X; KBr, paraffin oil; scan range 4000–400 $cm^{-1}$);
   X-ray powder diffraction pattern: see FIG. 6 (Scintag XDS 2000 powder diffractometer; Scintag, Santa Clara, Calif., USA); scan speed 0.5° or 1°/min (2 theta value);

2) Form B:
   m.p. determined by DSC (10° K/min): melting onset at about 159° C.;
   solubility (at 5° C.):
     water: 0.3 mg/ml
     methanol: 46.3 mg/ml
     ethanol: 18.1 mg/ml
     ethyl acetate: >50 mg/ml
     diethylether: 9.3 mg/ml;
     diisopropylether: 1.9 mg/ml
     hexane: 0.8 mg/ml;
   solubility (at 25° C.):
     water: 0.4 mg/ml
     methanol: >50 mg/ml
     ethanol: 34.4 mg/ml
     ethyl acetate: >50 mg/ml
     diethyl ether: 16.3 mg/ml
     diisopropyl ether: 3.1 mg/ml
     hexane: 1.5 mg/ml;
   solubility in the oil phase of TMF cream (oleyl alcohol/myglyol $812^R$ 4:6): 0.37%;
   chemical purity: 99.9%;
   thermogravimetry: loss of mass on drying up to melting: <0.05%;
   morphology (SEM): needles;
   hygroscopicity(uptake determined by thermogravimetry): 1 day, 92% r.h. and 1 week, 25° C., 75% r.h.: none;
   DSC curve: see FIG. 2 (Perkin-Elmer DSC-7; 40° C. to 200° C.; scan heating rate 10° K/min);
   FT-IR spectrum: see FIGS. 4 and 5 (PE FT-IR spectrometer 1725X; KBr; paraffin oil; scan range 4000–400 $cm^{-1}$);
   X-ray powder diffraction pattern: see FIG. 6 (Scintag XDS 2000 powder diffractometer); scan speed 0.5° or 1°/min (2 theta value).

3) For reference, the corresponding FT-IR spectrum of the amorphous form is indicated in FIG. 7.

Characterization data for all forms of the compound is further as follows:

optical rotation: $[\alpha]_D^{20}=-48.0°$ (±0.2°) (CDCl$_3$);
TLC:
R$_f$=0.18 (silicagel; hexane/ethyl acetate 2:1)
R$_f$=0.62 (silicagel; hexane/ethyl acetate 1:1);
$^1$H-NMR (CDCl$_3$): Two conformers (Z:E=1:2). Characteristic signals of the major conformer d [ppm]: 5.35 (d,J=1.7 Hz, H-26, 5.12 (d,J=9.0 Hz, H-29), 5.05 (d,J=9.4 Hz, H-20), 4.60 (d,J=5.0 Hz, H-2), 4.56 (m,w$_{1/2}$=10 Hz, H-33), 4.43 (d, J=13.8 Hz, H-6e), 3.66 (dd, J=9.6 Hz, J=1.0 Hz, H-14), 3.92 (m,H-24), 2.80 (dd, J=15.9 Hz, J=2.7 Hz, H-23a);
$^{13}$C-NMR (CDCl$_3$): Two conformers (Z:E=1:2). Signals of the major conformer d [ppm]: 213.7 (C-22), 196.3 (C-9), 169.1 (C-1), 164.8 (C-8), 138.8 (C-l9), 132.5 (C-28), 129.2 (C-29), 122.0 (C-20), 97.0 (C-10), 79.2 (C-32), 76.7 (C-26), 75.2 (C-15), 73.7 (C-14), 72.9 (C-13), 70.2 (C-24), 59.3 (C-33), 56.7 (C-2), 54.7 (C-21), 48.6 (C-18), 39.2 (C-6), 42.7 (C-23), 39.4 (C-25), 34.7 (C-30), 34.6 (C-11), 32.8 (C-12), 32.1 (C-35), 31.7 (C-34), 27.7 (C-3), 26.4 (C-17), 25.5 (C-31), 24.5 (C-5), 24.2 (C-36), 21.1 (C-4), 20.6 (17-Me), 16.2 (11-Me), 15.9 (19-Me), 14.2 (28-Me), 11.7 (C-37), 9.3 (25-Me).

In the above NMR spectra the carbon atom numbering is as appears in formula Ic hereafter:

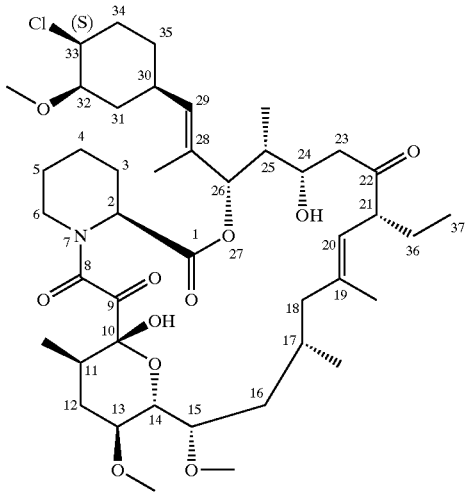

Ic

Abbreviations
DMSO: dimethylsulfoxide
DSC: differential scanning calorimetry
FT-IR: Fourier transformed infrared
m.p.: melting point
r.h.: relative humidity
SEM: scanning electron microscopy
T: transmission
TG: thermogravimetry
THF: tetrahydrofuran
TLC: thin layer chromatography

Figure 1:
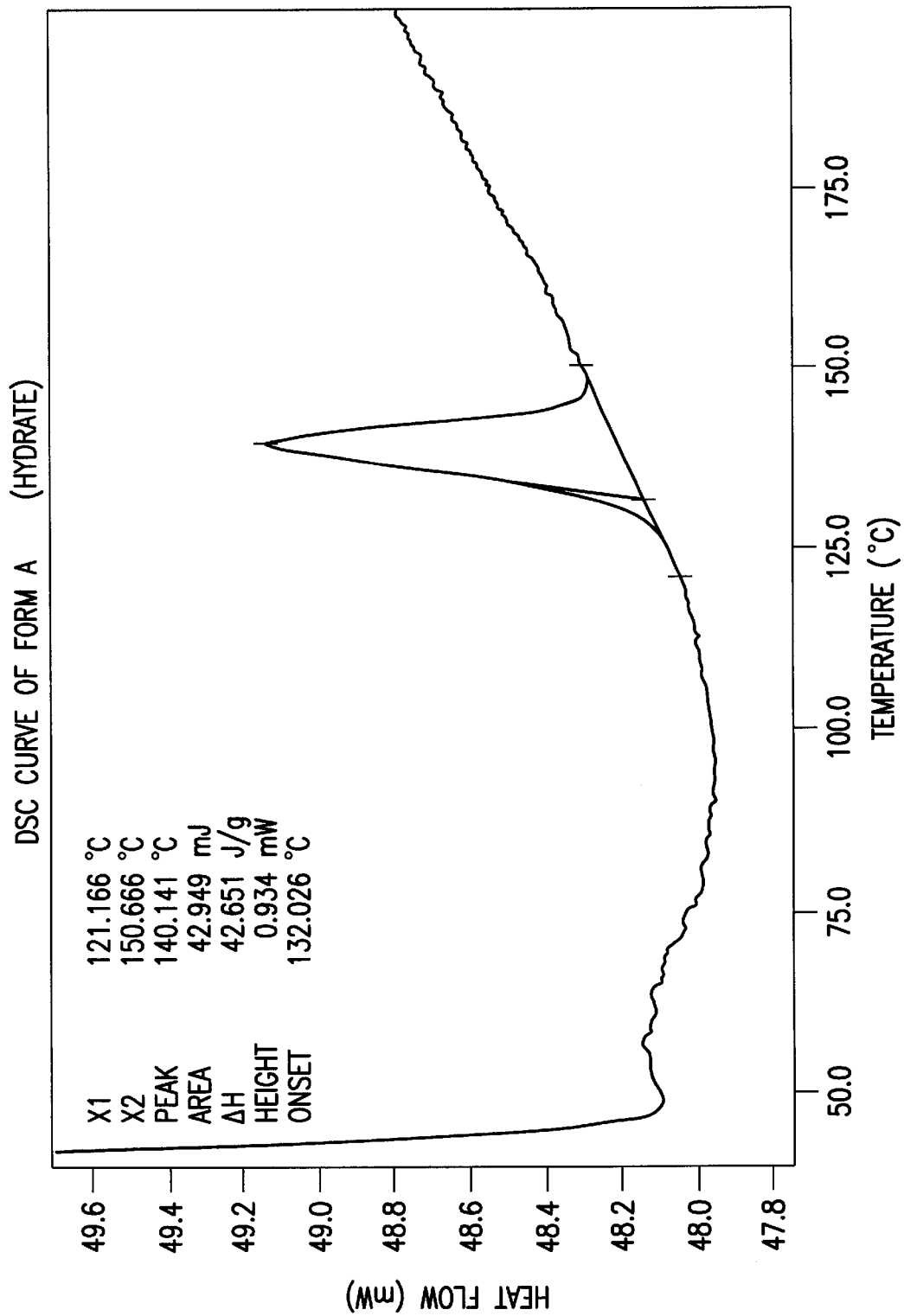
FIG. 1: DSC curve of Form A (hydrate)
Figure 2:
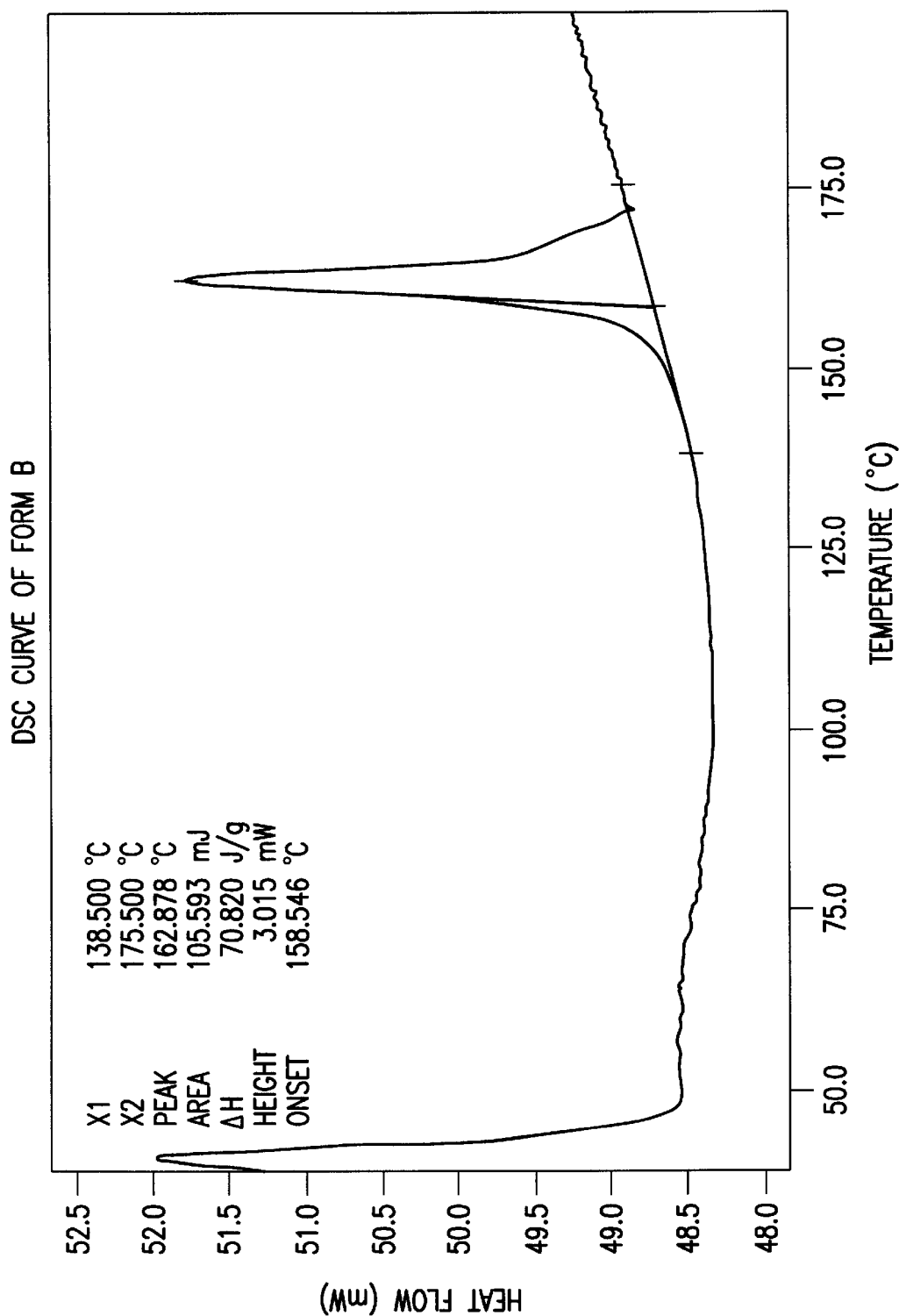
FIG. 2: DSC curve of Form B (anhydrous)
Figure 3:
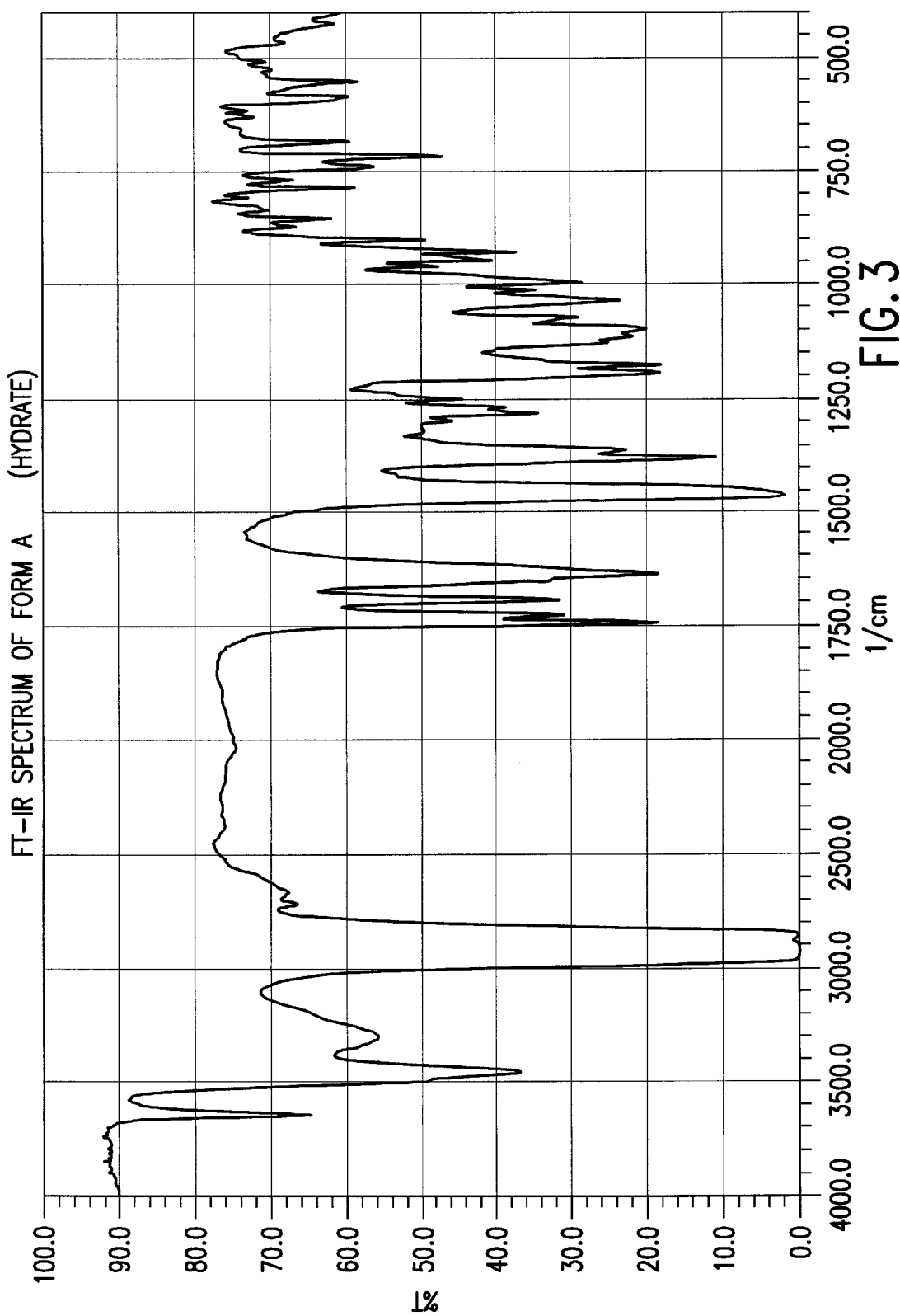
FIG. 3: FT-IR spectrum of Form A (hydrate) (% T=percentage transmission)
Figure 4:
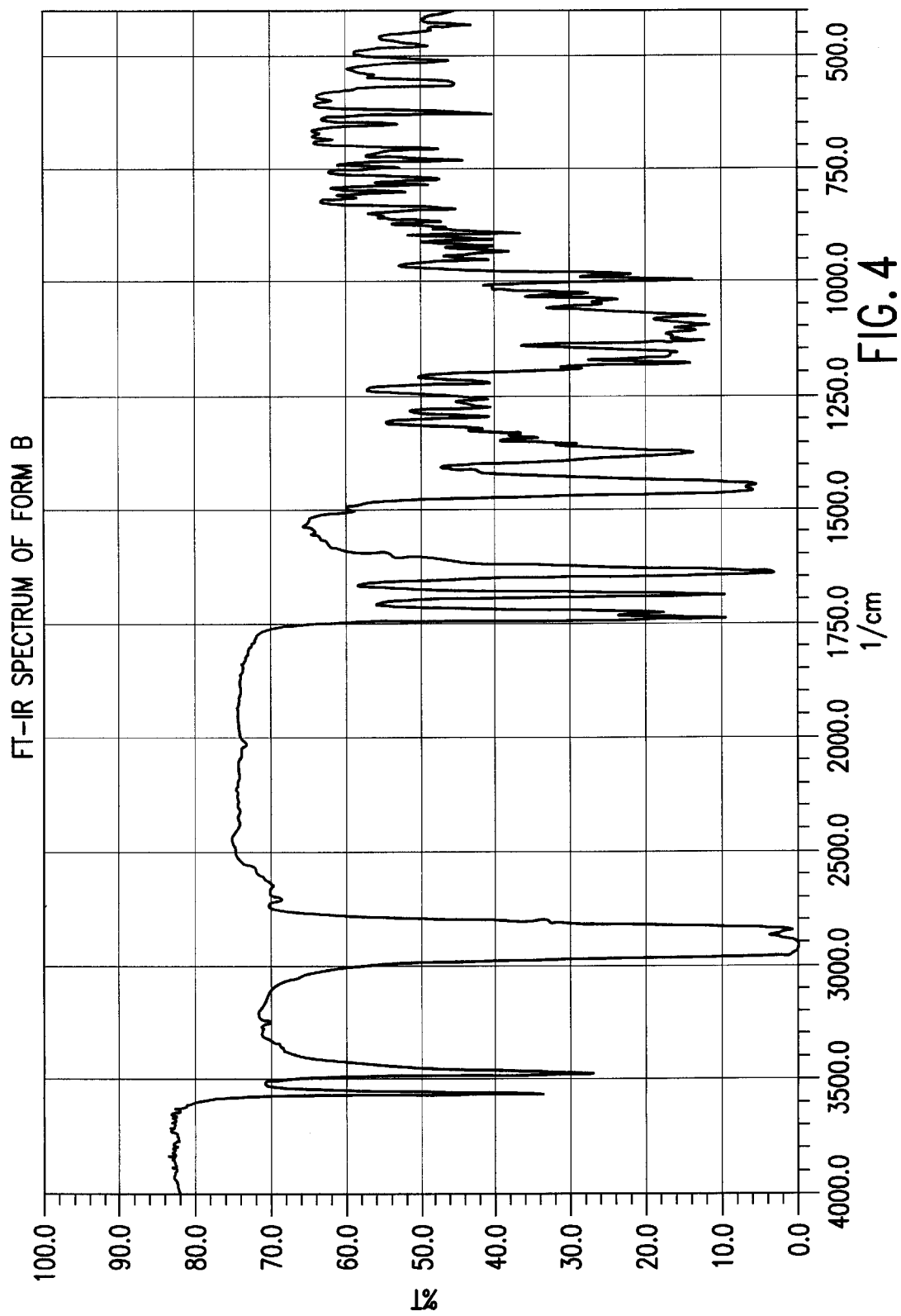
FIG. 4: FT-IR spectrum of Form B (% T=percentage transmission)
Figure 5:
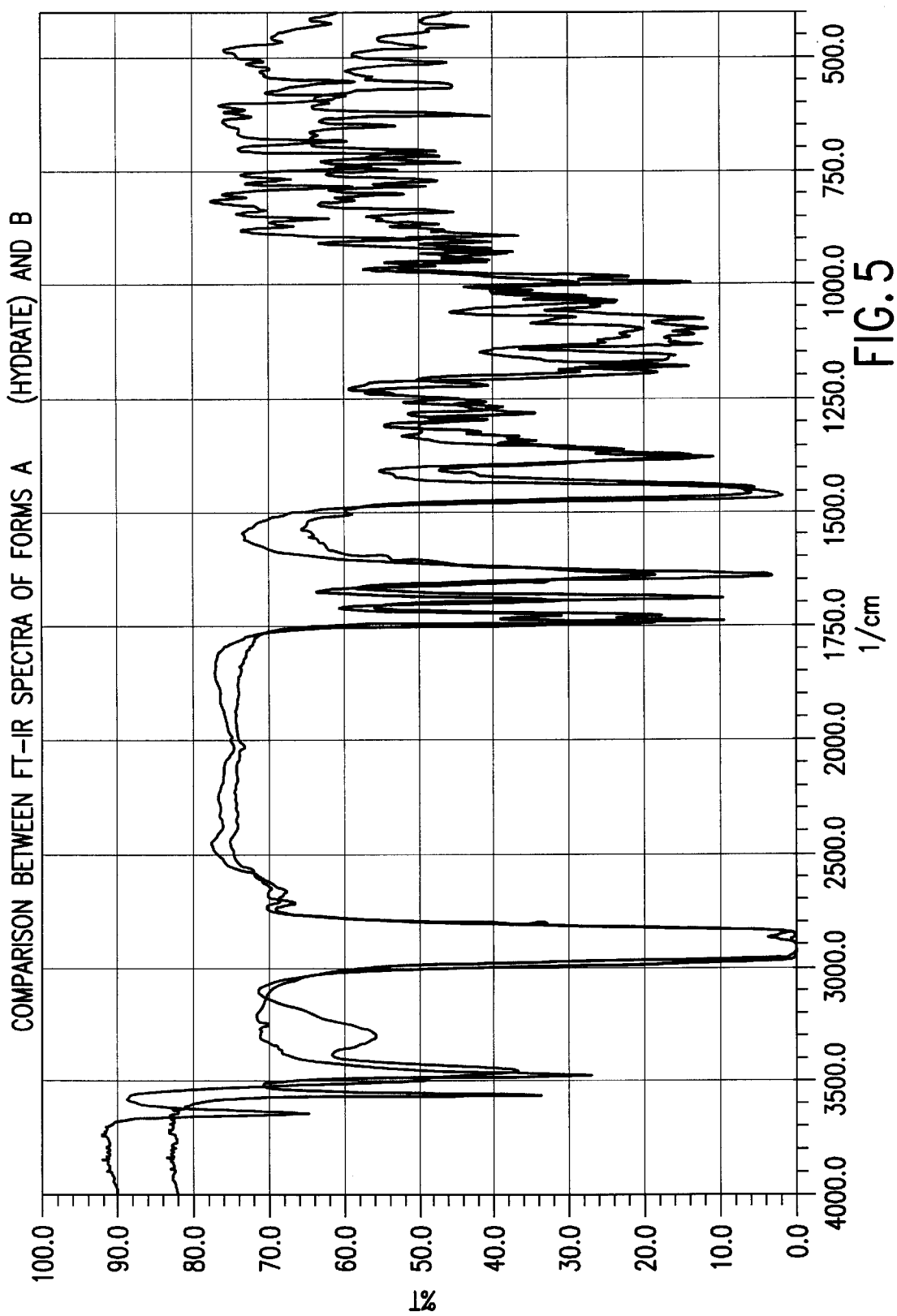
FIG. 5: Comparison between FT-IR spectra of forms A (hydrate) and B (% T=percentage transmission) Form A (hydrate)=graph starting at 90% T Form B=graph starting at 82% T
Figure 6:
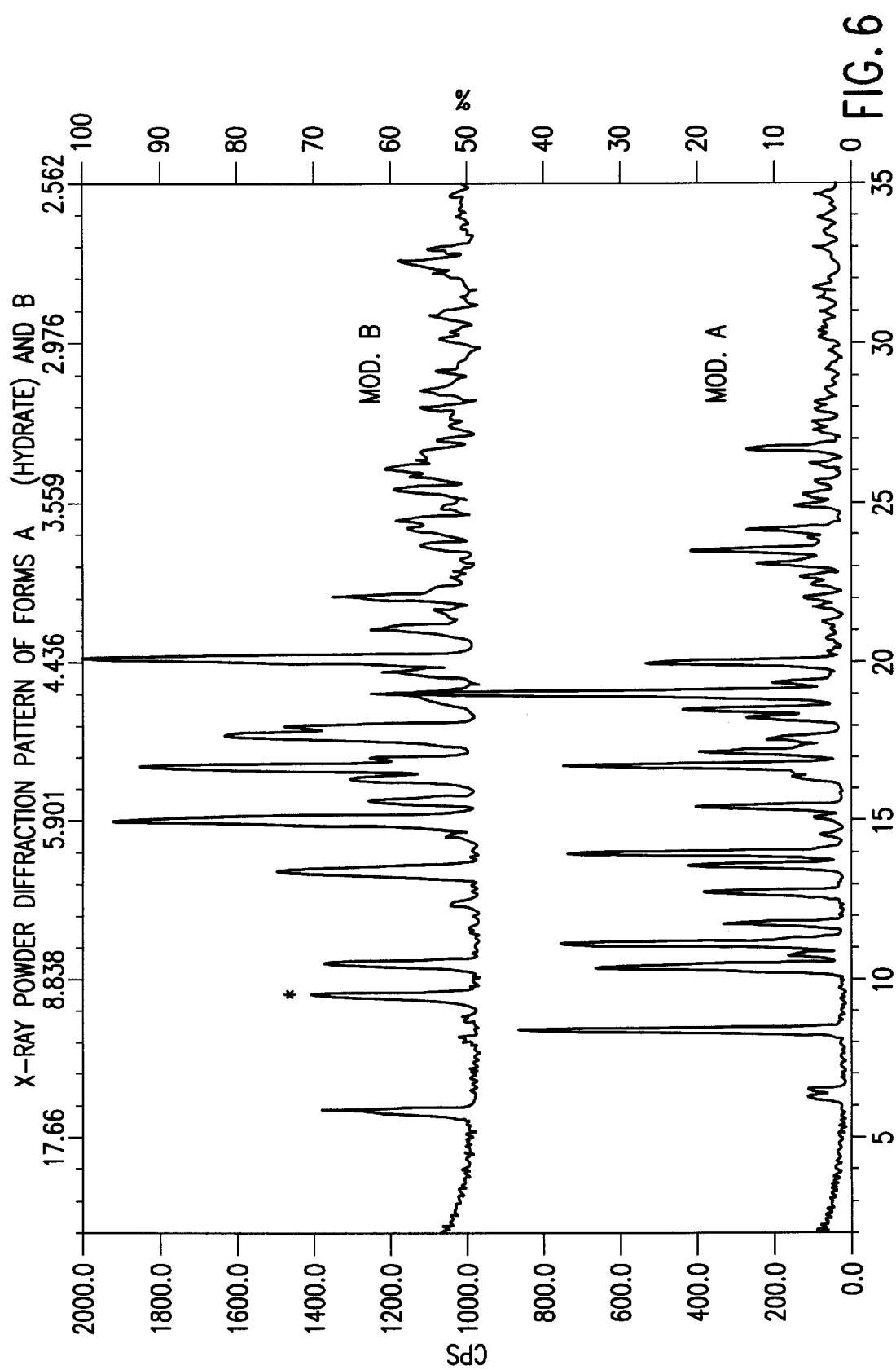
FIG. 6: X-ray powder diffraction pattern of forms A (hydrate) and B Mod. A=Form A (hydrate) Mod. B=Form B left ordinate: intensity (cps=counts per second) right ordinate: relative intensity (%=percentage) top abscissa: resolution bottom abscissa: 2 theta angle (degree)
Figure 7:
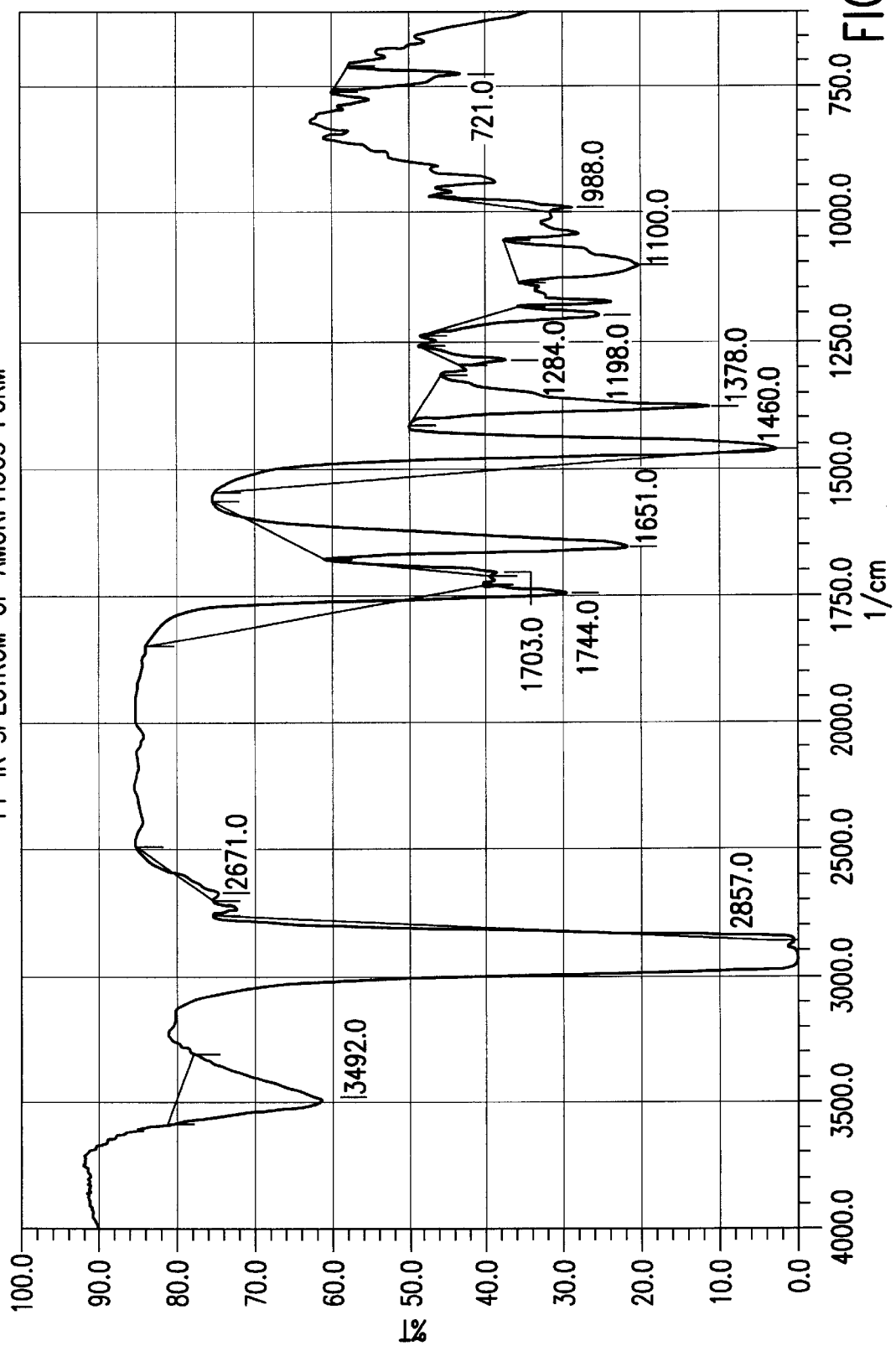
FIG. 7: FT-IR spectrum of amorphous form (%=percentage transmission)

The compound of formula I in amorphous form is known as a pharmaceutical, in particular for use as an anti-inflammatory, immunosuppressant and antiproliferative agent, both systemically or topically. The preparation of suitable galenical forms for pharmaceutical use, such as creams, emulsions and ointments is, however, difficult. Thus the amorphous form of the compound suffers from problems of instability, such as in bulk, and is generally not well-suitable for galenical processing compared to an exactly defined, crystalline form, e.g. as regards degradation of the bulk material, hygroscopicity, dissolution properties, and overall purity of the material.

The availability of well-defined crystalline forms of the compound of formula I is therefore particularly indicated for use in the preparation of galenical forms of the compound where it is indicated to overcome the above disadvantages, such as in the preparation of topical forms, e.g. creams, emulsions and ointments where it is desired to include the compound normally in dissolved state but under carefully controlled conditions. Thus in the preparation of a cream, it has been observed that Form A dissolves in the oil phase in about 10 minutes, whereas for Form B it takes about 6 hours. It is therefore very advantageous to use crystalline product of well-defined characteristics, whereby Form A or Form B is preferably employed, depending on the particular application, e.g. Form A where a lower melting point or more pronounced solubility is desired, or Form B where a higher melting point, or thermodynamically more stable product at room temperature is appropriate.

Beneficial effects gained with the crystalline form are e.g.:
less solvent residue in the ultimate drug substance in whatever form, such as dissolved state;
additional purification effect obtained by crystallization;
higher stability of the drug substance; and
easier handling in the production plant.

The compound of formula I in crystalline form may be formulated for administration in any convenient way. It preferably is in dissolved state in the ultimate galenical form.

The invention thus also includes pharmaceutical compositions comprising, or whenever prepared from, the compound of formula I or a tautomeric or solvated form thereof, in crystalline form, such as Form A and Form B. It also includes the compound of formula I or a tautomeric or solvated form thereof, in crystalline form for use as a pharmaceutical, or for use in the preparation of a medicament with anti-inflammatory, imunosuppressant and anti-proliferative activity.

The following Examples illustrate the invention but are not limitative. All temperatures are in degrees Centigrade unless indicated otherwise.

EXAMPLE 1

Crystalline 33-epichloro-33-desoxyascomycin
(Form A)
(from a solution of amorphous product in ethanol)

To a solution of 27 g amorphous 33-epichloro-33-desoxyascomycin (colourless foamy resin) in 180 ml of ethanol at room temperature is carefully added water until a transient cloudiness appears (approximately 65 ml of water). The solution is left undisturbed for 16 hours at 4°. Colourless crystals are formed. 10 ml of water are added and the mixture is left undisturbed for another 4 hours at 4°. The crystalline material is separated by suction, washed with an ice-cold mixture of ethanol and water 1:1 (v/v), and dried under reduced pressure (12 mm Hg) for 20 hours at room temperature. The title compound is obtained (yield 18 g; m.p. 135–136°; chemical purity $\geq$98%, i.e. impurity level at or below analytically detectable limits upon HPLC; hydrate).

EXAMPLE 2

Solubilization of Forms A and B in 1% creams a) The solubility of Form A in a cream formulation is estimated to be about 1% at room temperature. In the manufacturing of cream, the drug substance is completely dissolved in the oily phase at 60–75°. To assess whether and after which storage time part of the drug substance dissolved will crystallize from the 1% cream, a series of batches is examined for crystals. The investigation of 10 batches shows that no crystals are observed after manufacturing as well as after storage at 5°, 25°, and 40°. Even in the samples which are subjected to a temperature cycling test for about 3 months no crystals are detected. Only in one preformulation (1%) drug substance crystals very sparsely occurred after one-year-storage at 25°, which indicates that the 1% cream is at the borderline with respect to saturation with drug substance.

The drug substance used in the batches and preformulations mentioned above contained 100% Form A.

b) To assess whether drug substance containing Form B can be completely dissolved in the manufacturing of cream and to evaluate the long-term crystallization behaviour, several preformulations (cream, 1%) containing 0%, 1%, 5% and 10% Form B relative to the total content of compound of formula I are manufactured and put on stability testing at different temperatures.

During the preparation of these preformulations, it is observed that the solving speed of crystal Form B in the oily phase of the cream is much slower than that of crystal Form A. Immediately after manufacturing, the forms are investigated and no remaining crystals are observed.

To get information about the long-term crystallization behaviour of these forms, the stability samples are further investigated after 6 weeks, 3, 6 and 9 months storage. The results show that no crystals form even upon prolonged storage.

EXAMPLE 3

Crystalline form A of 33-epichloro-33-desoxyascomycin
(from a solution in ethanol/isopropanol/water)

10 g of 33-epichloro-33-desoxyascomycin Form B (or, alternatively, crude Form A, or amorphous material) are dissolved 1:5 (w/w) in 10 g of a mixture of ethanol/isopropanol/water 9:0.5:0.5 (v/v) at 70° and the mixture is submitted to clear filtration on a 0.5 μm filter. The resultant solution free of crystallization germs is allowed to cool to 10°, water is added (25% w/w based on amount of product) to supersaturate the solution. Seeding is effected with 0.06 g of crystals of Form A (following checking with a thermal microscope) and water is carefully added (7.5 times excess based on the amount of product) over a period of 4 hours at 100, and thereafter the solution is stirred for 2 hours at that temperature. The title compound is obtained (hydrate; 9.3 g).

It is desirable to seed with crystals of Form A as crystallographically pure as possible. Thus seeding with crystals of Form A containing 2% crystals of Form B as impurity can lead to recovery of crystals of Form A containing 20% crystals of Form B as impurity. However, at low temperature the formation of the thermodynamically more stable Form B is clearly inhibited: thus seeding at 0° with a 1:1 mixture of both Forms A and B results in a product containing 75% of Form A.

EXAMPLE 4

Crystalline form B of 33-epichloro-33-desoxyascomycin
(from a solution in ethanol/isopropanol/water)

25 g of 33-epichloro-33-desoxyascomycin Form A (hydrate) (or, alternatively, crude Form B, or amorphous material) are dissolved 1:7 (w/w) in 75 g of a mixture of ethanol/isopropanol/water 9:0.5:0.5 (v/v) at 70° and the mixture is submitted to clear filtration. The resultant solution is allowed to cool to 30°, and optionally seeded with 0.1 g of crystals of Form B. Water (3.5 times excess based on the amount of product) is carefully added over a period of 4 hours; the title compound is obtained (24.6 g).

EXAMPLE 5

Crystalline form A of 33-epichloro-33-desoxyascomycin
(from a solution of crude product in acetone)

A solution of 94.5 g of crude 33-epichloro-33-desoxyascomycin (e.g. as obtained following chromatography) (containing various amounts of Form A and/or Form B and/or amorphous product) in 1500 ml of acetone is evaporated at 48–52° (400–50 mbar). The resultant amorphous foam is dissolved in 500 ml of ethanol/isopropanol 9.5:0.5 (v/v). The solution is evaporated at 48–52° (400–50 mbar). The resultant foam is dissolved in 400 ml of ethanol/isopropanol 9.5:0.5 (v/v) and the hot solution (70–75°) is filtered on a 0.45 μm filter. The solution is cooled to 20–25° over 30–40 minutes, 200 ml of water is added and the mixture is seeded with Form A crystals. Stirring is continued for 1 hour at 20–25°. A suspension is formed which is cooled to 0–5° and further stirred for 4 hours. The crystals are filtered and washed with 300 ml of precooled ethanol/water 1:3 (v/v). Drying at 45–50° (10–20 mbar, 16 hours) gives the title compound (hydrate; colourless crystals).

EXAMPLE 6

Crystalline form A of 33-epichloro-33-desoxyascomycin
(from a solution of Form B in acetone)

94.5 g of 33-epichloro-33-desoxyascomycin Form B are dissolved in 1500 ml of boiling acetone. The acetone solution (now free of any seeds of Form B) is then treated as described in Example 5 above. The title compound is obtained (hydrate; colourless crystals).

What is claimed is:

1. The compound of formula I

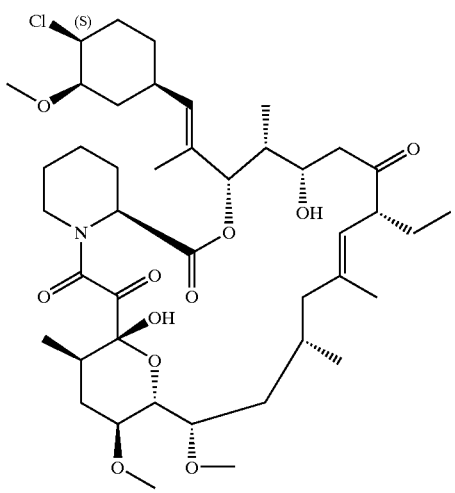

or a tautomeric or solvated form thereof, in crystalline form.

2. The compound according to claim 1 in crystalline Form A.

3. The compound according to claim 1 in crystalline Form B.

4. A process for the preparation of a crystalline compound according to claim 1 which comprises appropriately converting amorphous compound of formula I from a solution thereof under crystallization-inducing conditions.

5. A process for the preparation of the crystalline compound according to claim 2 which comprises appropriately converting compound of formula I in other than Form A, or a tautomeric or solvated form thereof, from a solution thereof under conditions inducing preferential crystallization of Form A.

6. A process for the preparation of the crystalline compound according to claim 3 which comprises appropriately converting compound of formula I in other than Form B, or a tautomeric or solvated form thereof, from a solution thereof under conditions inducing preferential crystallization of Form B.

7. A pharmaceutical composition comprising a compound according to claim 1.

8. A method of treating inflammation or inducing immunosuppression or inhibiting cell proliferation, comprising administering to a patient in need of said treating a therapeutically effective amount of a compound according to claim 1.

* * * * *